(12) United States Patent
Eidler et al.

(10) Patent No.: US 9,364,395 B2
(45) Date of Patent: Jun. 14, 2016

(54) CARTRIDGE SYRINGE

(75) Inventors: Josef Eidler, Schwanenstadt (AT); André Carnal, Solothurn (CH)

(73) Assignee: CAMO Formen- Und Werkzeugbau GmbH, Schwanenstadt (AT)

( * ) Notice: Subject to any disclaimer, the term of this patent is extended or adjusted under 35 U.S.C. 154(b) by 454 days.

(21) Appl. No.: 14/001,240

(22) PCT Filed: Feb. 10, 2012

(86) PCT No.: PCT/EP2012/052306
§ 371 (c)(1),
(2), (4) Date: Oct. 22, 2013

(87) PCT Pub. No.: WO2012/113661
PCT Pub. Date: Aug. 30, 2012

(65) Prior Publication Data
US 2014/0299228 A1    Oct. 9, 2014

(30) Foreign Application Priority Data

Feb. 23, 2011   (DE) .................. 10 2011 012 108

(51) Int. Cl.
| | | |
|---|---|---|
| *B65B 1/04* | (2006.01) | |
| *A61J 1/20* | (2006.01) | |
| *A61M 5/24* | (2006.01) | |
| *A61M 5/315* | (2006.01) | |

(52) U.S. Cl.
CPC ............ *A61J 1/2096* (2013.01); *A61M 5/24* (2013.01); *A61M 5/31515* (2013.01); *A61J 1/201* (2015.05); *A61J 1/2048* (2015.05)

(58) Field of Classification Search
CPC .......... A61M 5/24; A61M 2005/2414; A61M 5/31515
USPC ........................................................... 141/27
See application file for complete search history.

(56) References Cited

FOREIGN PATENT DOCUMENTS

| EP | 0170009 A1 | 2/1986 |
| GB | 2445228 A | 7/2008 |
| WO | 02/04049 A1 | 1/2002 |
| WO | 03/101527 A1 | 12/2003 |

OTHER PUBLICATIONS

International Search Report for PCT/EP2012/052306 dated May 3, 2012.

*Primary Examiner* — Jason K Niesz
(74) *Attorney, Agent, or Firm* — Thompson Coburn LLP

(57) ABSTRACT

A cartridge syringe has a housing with an opening for inserting the cartridge having a cylinder filled with a medication and closed at its ends by a piercing membrane and a stopper having a blind hole. A ram is provided for pressing the stopper for injecting the medication in the cylinder after piercing the membrane. The ram has an actuating element and can be attached in the blind hole of the stopper for aspiration. The ram has an outer sleeve with a core. The outer sleeve is displaceably guided in a rotatable manner and the core in a rotationally fixed manner. A front end of the outer sleeve is provided with at least one fixing hook which is spring-loaded inwardly A cam is engageable with the fixing hook such that, upon rotation of the outer sleeve, the fixing hook is movable either to the fixing position or to the unlocked position.

8 Claims, 3 Drawing Sheets

CARTRIDGE SYRINGE

CROSS-REFERENCE TO RELATED APPLICATIONS

This application is a national stage application filed pursuant to the Patent Cooperation Treaty related to application PCT/EP2012/052306, published as WO2012/113661, which was filed Feb. 10, 2012, which claims priority to DE 10 2011 012 108.0, filed Feb. 23, 2011, the disclosures all of which are incorporated by reference herein.

BACKGROUND AND SUMMARY

The invention relates to a cartridge syringe according to the preamble of claim 1.

Cartridge syringes of metal, which must be sterilised, logged and packed in blister packs again after application and before re-use, are used almost exclusively in the field of dentistry. This involves considerable effort. In addition, there is the risk that the sterilisation is not carried out properly and thus contaminated syringes are used.

Therefore, the object of the invention is to provide a cartridge syringe which may be configured as a disposable syringe easy to manufacture, rendering sterilisation after use unnecessary.

This is achieved by the cartridge syringe characterised in claim 1.

This means that, according to the invention, the ram consists of an outer sleeve in which a core is disposed. Although the outer sleeve and the core can jointly be moved, the outer sleeve is rotatable relative to the receptacle housing, whereas the core is connected to the rear end of the receptacle housing in a rotationally fixed manner.

At the rear end of the outer sleeve and thus of the ram, an actuating element such as a ring or a plate is provided, for example for the user's thumb.

In order that the syringe may be used for aspiration, i.e. for aspirating body fluids by means of the injection cannula attached to the front end of the receptacle housing, the stopper by which the ampule cylinder is closed has a blind hole, with the front end of the outer sleeve fixable in the blind hole engaging therewith.

According to the invention, the front end of the outer sleeve has, for this purpose, at least one fixing hook spring-loaded inwardly, thus relative to the longitudinal axis of the ram, which is movable between a fixing position in the blind hole of the stopper directed outwardly sideways and an inwardly directed unlocked position.

The blind hole in the stopper may have a smooth bore wall. Preferably, however, it is provided with at least one annular groove or internal thread, the at least one fixing hook engaging therewith in the fixing position.

In order to move the fixing hook from the fixing position to the unlocked position and vice versa, a cam is provided at the front end of the core, engaging with the fixing hook such that, upon rotation of the outer sleeve, the fixing hook is movable either to the fixing position or to the unlocked position. Thus, the fixing hook is spring-loaded towards the cam.

Preferably, the cam is elliptical in cross section. The fixing hooks rotated to the major axis of the ellipse assume the fixing position, whereas they are in the unlocked position when being rotated to the minor axis of the ellipse.

That is to say the two fixing hooks are spread apart by means of the cam being elliptical in cross section in order to engage with the bore wall and/or the annular groove or the internal thread in the blind hole of the stopper when the two fixing hooks are rotated to the major axis of the ellipse, whereas, as a result of their being spring-loaded, the two fixing hooks are moved towards each other in the minor axis of the ellipse in the unlocked position so that they are disengaged from the bore wall of the blind hole in the stopper with the result that, after pulling out the extension from the blind hole, the cartridge may be removed from the lateral longitudinal opening of the receptacle housing after use.

Preferably, a slotted guide is provided for the rotation of the outer sleeve. The slotted guide may be formed by means of a recess in the outer sleeve, for example a groove on the outside of the outer sleeve or a slot in the outer sleeve, with a protrusion attached to the rear end of the receptacle housing engaging with the recess.

The recess may consist, for example, of two sections extending along the outer sleeve and being connected to each other by means of an inclined section.

For guiding the core disposed in the outer sleeve in a rotationally fixed manner, a rib extending in the longitudinal direction may be provided on the core, with said rib being guided on both sides by means of protrusions at the rear end of the receptacle housing. Instead, a longitudinal recess, for example a longitudinal groove, may be provided in the core, with a protrusion attached to the rear end of the receptacle housing engaging therewith.

In order to hold the syringe with the forefinger and the middle finger, the receptacle housing preferably has a plate-shaped enlargement at its rear end. Preferably, a thread is provided at the front end of the receptacle housing in order to attach the piercing cannula for piercing the piercing membrane of the cartridge extending into the receptacle housing and the injection cannula, with both cannulas preferably forming a unit.

In order that the cartridge syringe according to the invention can be used as a disposable syringe, it is preferably made of a plastic material and preferably manufactured using a multi-component in-mould assembly process.

An injection moulding die with a plurality of injection moulding units, for example four injection moulding units, may be used, each having a plurality of mould cavities.

Preferably, the injection moulding die is moved by rotation about at least three stations, wherein the receptacle housing and the actuating element are injection-moulded at the first station and, at the second station, the outer sleeve connecting the receptacle housing to the actuating element, whereas, at the third station, the core is injected into the outer sleeve, namely with a plastic material which does not adhere to the plastic material of the outer sleeve, thus, in particular, does not react with the plastic material of the outer sleeve.

Preferably, a fourth station is provided, from which the finished syringes are removed, whereupon they are wrapped in foil by a packaging machine, for example.

Injection moulding at the individual stations and/or removal of the syringes from the fourth station take place simultaneously. Preferably, the injection moulding die is moved by rotation from one station to the other.

The invention will be described in more detail below by way of example with reference to the accompanying drawings, in which:

FIG. 1 shows a perspective view of the cartridge syringe;

FIGS. 2 and 3 each show the rear parts of the receptacle housing as well as the front part of the ram with the spring-loaded fixing hook on the outer sleeve in the unlocked position and the spread apart fixing position respectively;

Figure 8:
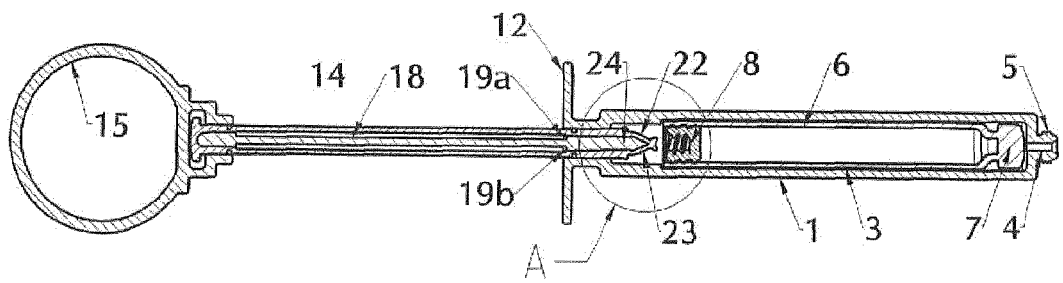
Figure 9:
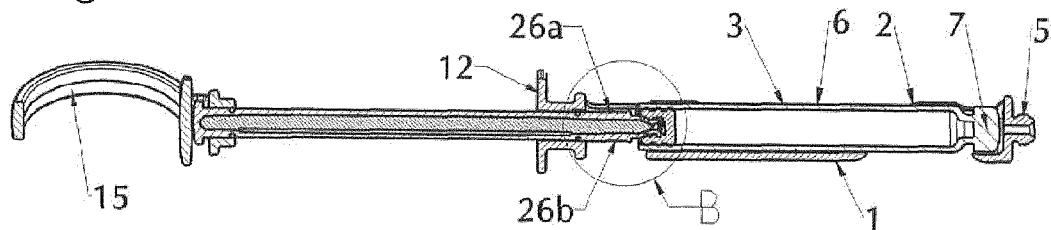
Figure 10:
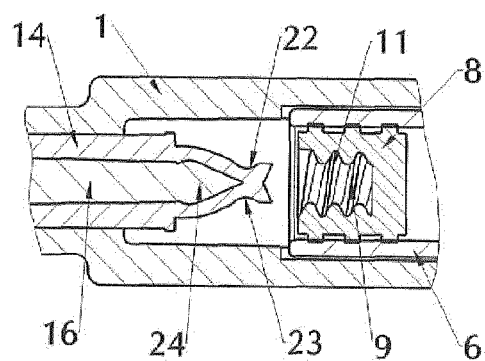
Figure 11:
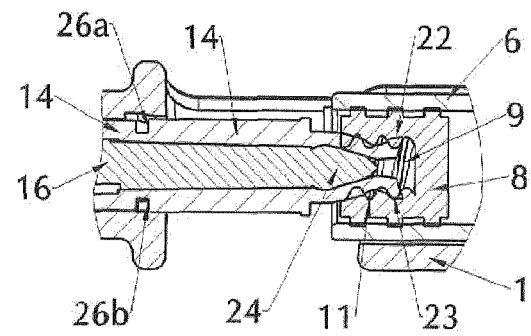
Figure 12:
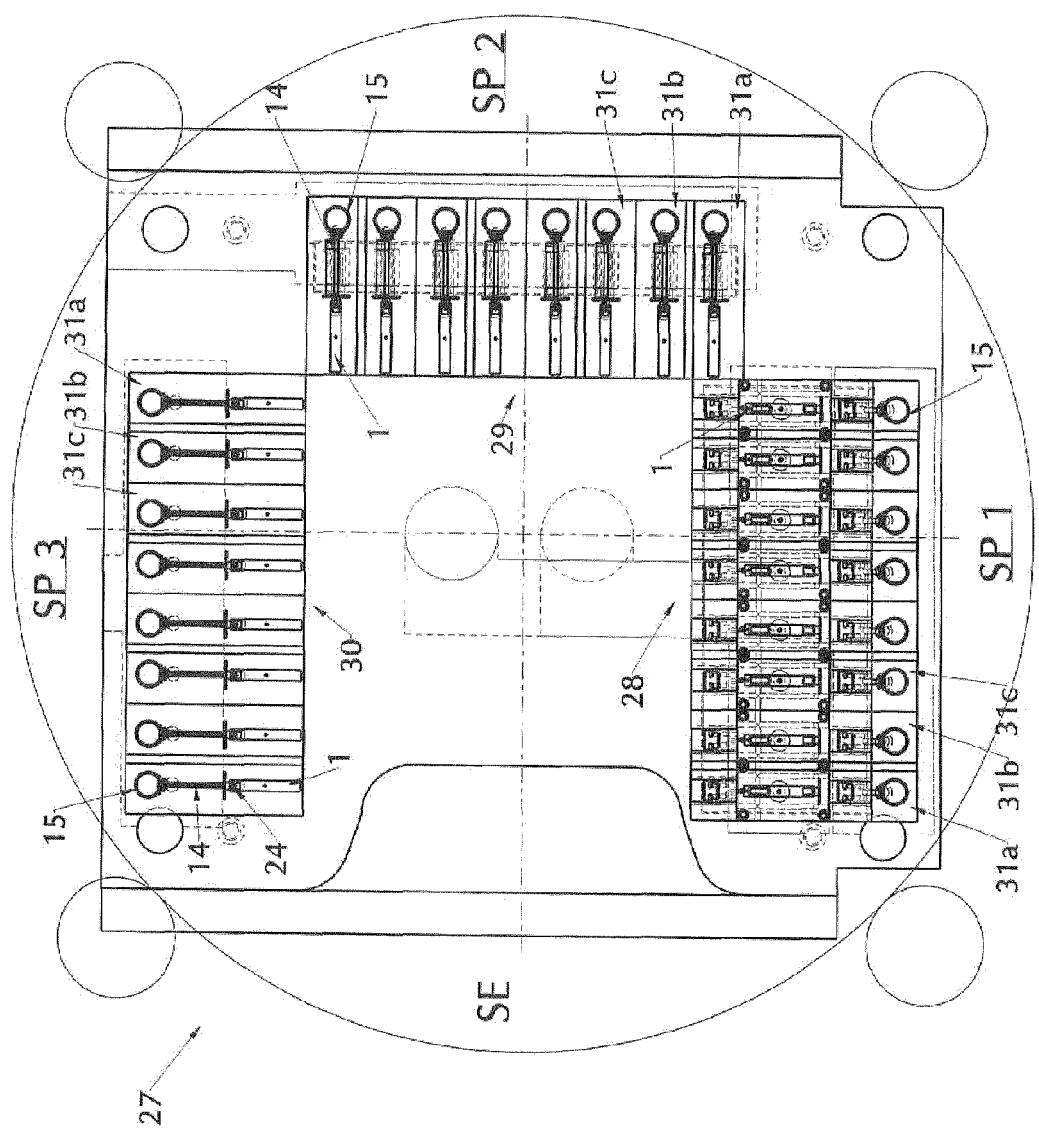

FIGS. 8 and 9 each show a longitudinal section through the cartridge syringe with the fixing hook in the unlocked position and the fixing position respectively;

FIGS. 10 and 11 show an enlarged view of sections A and B respectively in FIGS. 8 and 9; and FIG. 12 shows a top view of the injection moulding die for manufacturing the cartridge syringe.

According to FIGS. 1, 4, 7, 8 and 9, the cartridge syringe has a cylindrical receptacle housing 1 provided with a lateral longitudinal opening 2 for inserting the cartridge into the receptacle housing 1.

At the front end of the receptacle housing 1, an axial bore 4 with a thread 5 is provided for screwing on a unit (not shown) consisting of a piercing cannula extending through the bore 4 into the receptacle housing 1 and an injection cannula.

The cartridge 3 is formed by means of an ampule cylinder 6 filled with a medication, a piercing membrane 7 at the front end and a stopper 8 at the rear end.

When inserting the cartridge 3 into the receptacle housing 1, the piercing membrane 7 is pierced by the piercing cannula (not shown) attached to the thread 5.

The stopper 8 has a blind hole 9 provided with an internal thread 11 or suchlike grooves on the circumference.

At the rear end of the receptacle housing 1 provided with a plate-shaped enlargement 12, a ram 13 is displaceably guided. For injecting the medication, the latter is pressed out of the ampule cylinder 6 by means of the ram 13 via the piercing cannula (not shown) and the injection cannula (not shown) with the stopper 8 attached thereto.

Figure 7:
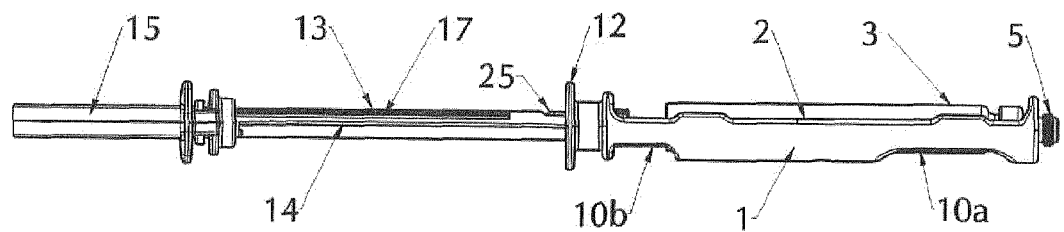
FIG. 7 shows a lateral view of the cartridge syringe.

The ram 13 comprises an outer sleeve 14 to which the actuating element 15 configured as a ring, for example, as well as a core 16 being disposed in the outer sleeve 14. The outer sleeve 14 is rotatable about its longitudinal axis relative to the receptacle housing 1. For this purpose, it is provided with a rough surface structure, for example a fluting 17. On the side opposite to the longitudinal opening 2, the receptacle housing 1 has two windows 10a, 10b at the front end portion and the rear end portion respectively (FIG. 7).

Even though the core 16 is displaceably guided together with the outer sleeve 14 at the rear end of the receptacle housing 1, it is arranged in a rotationally fixed manner, thus, contrary to the outer sleeve 14, not rotatable relative to the receptacle housing 1.

For this purpose, the core 16 has a longitudinally extending rib 18 which is guided on both sides by means of pencil-shaped protrusions 19a, 19b attached to the rear end of the receptacle housing 1 on a level with the enlargement 12 (FIG. 8).

Figure 3:
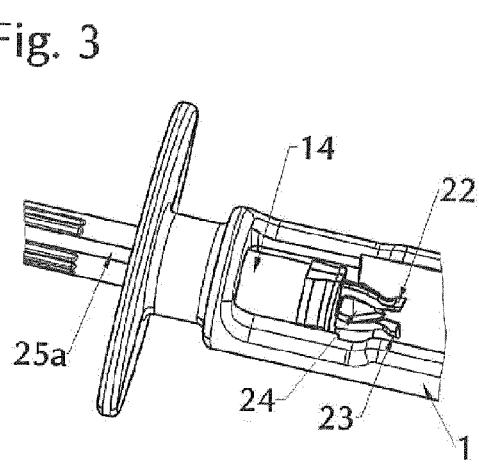
Figure 4:
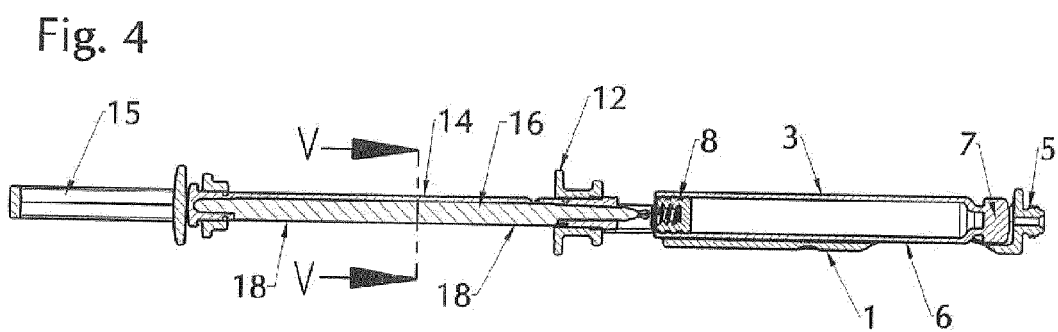
FIG. 4 shows a longitudinal section of the cartridge syringe.
Figure 5:
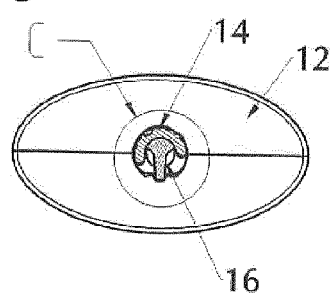
FIG. 5 shows a section along the line V-V in FIG. 4.
Figure 6:
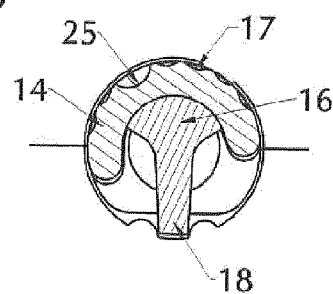
FIG. 6 shows an enlarged view of section C in FIG. 5.

For aspiration, the front end of the outer sleeve 14 has as an extension two fixing hooks 22, 23 which are spring-loaded inwardly, thus towards each other, and which are movable between a fixing position being directed outwardly sideways, thus spread apart, (FIGS. 3 and 7) and an inwardly directed unlocked position (FIGS. 10 and 11).

For moving the fixing hooks 22, 23 to the fixing position and the unlocked position and vice versa, a cam 24 is provided at the front end of the core 16.

The cam 24 tapering towards the front is elliptical in cross section. When the fixing hooks 22, 23 are rotated to the major axis of the ellipse by rotation of the outer sleeve 14, the fixing hooks 22, 23 are spread apart such that they engage with the thread groove of the internal thread 11 (FIGS. 9 and 11), whereas, when the outer sleeve 14 is rotated relative to the core 16 such that the fixing hooks 22, 23 abut the cam 24 in the minor axis of the ellipse, the fixing hooks 22, 23 can be disengaged from the thread groove of the internal thread 11 (FIGS. 8 and 10).

In order to rotate the outer sleeve 14 through 90 degrees relative to the core 16, thus in such a way that the fixing hooks 22, 23 are moved on the cam 24 from the major axis to the minor axis of the ellipse and vice versa, a slotted guide is provided.

Figure 1:
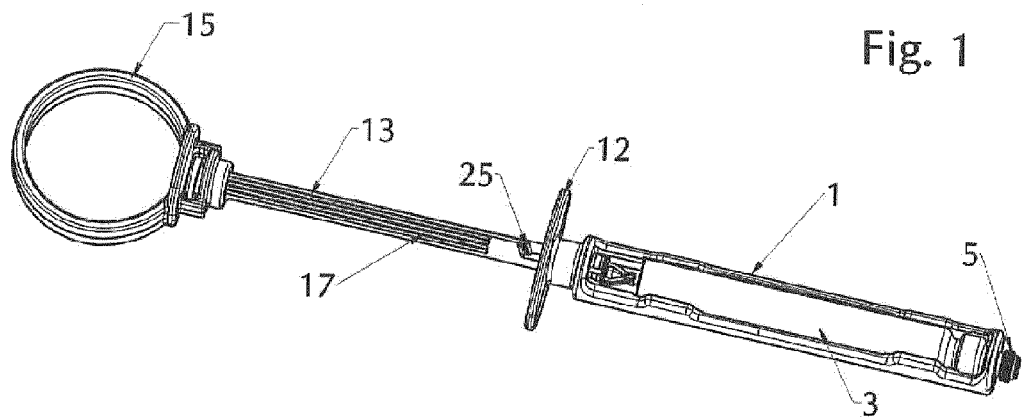
Figure 2:
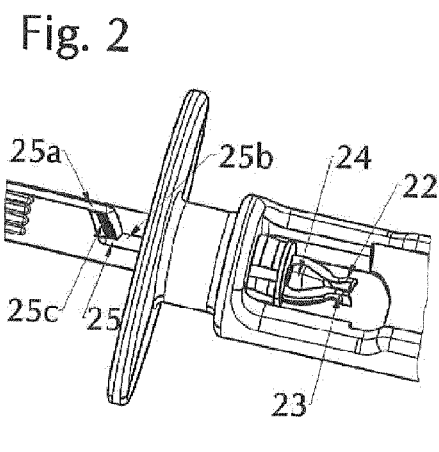

As shown in FIG. 2, for example, the slotted guide consists of one external groove 25 on either side of the outer sleeve 14 respectively. As can be seen from the one groove 25 shown in FIG. 2, the groove 25 consists of two sections 25a, 25b running parallel in the longitudinal direction and being connected by an inclined section 25c.

A pencil-shaped protrusion 26a, 26b attached to the receptacle housing 1 engages with the groove 25 or each groove 25 respectively (FIGS. 9 and 11).

The cartridge syringe according to the invention is made of a plastic material using injection moulding.

A multi-component in-mould assembly process is applied, using the injection moulding die 27 used in FIG. 12.

The injection moulding die 27, which is rotatable about an axis perpendicular to the plane of projection, consists of four injection moulding units, each being provided with a plurality of mould cavities 31a, 31b, 31c . . . , for example eight mould cavities. The drawing shows only three injection moulding units 28, 29, 30, whereas the fourth injection moulding unit is arranged behind the injection moulding unit 28.

At the injection station SP1, the receptacle housing 1 with the thread 5, the enlargement 12 and the protrusions 19a, 19b, 26a, 26b as well as the ring-shaped actuating element 15 are injection-moulded in the injection moulding unit 28 and the injection moulding unit arranged behind it (not shown).

At the second station SP2, the outer sleeve 14 provided with the spring-loaded fixing hooks 22, 23 and connecting the receptacle housing 1 to the actuating element 15 is injection-moulded in the injection moulding unit 29. During this process, the outer sleeve 14 is injection-moulded from a plastic material which does not adhere to the plastic material of which the receptacle housing 1 and the actuating element 15 are made.

At the third station SP3, the core 16 with the rib 18 and the cam 24 at the front end is injection-moulded in the injection moulding unit 30, namely from a plastic material which does not adhere to the plastic material of which the outer sleeve 14 is made.

At the station SE, the finished cartridge syringes are removed and supplied to a packaging unit (not shown) for sterile packaging.

Thus, the injection moulding die 27 is rotated through 90 degrees after each injection moulding step.

It is also apparent that, according to the invention, the multi-component in-mould assembly can be carried out with only two components or plastic materials if required, namely with one component for the core 16, the receptacle housing 1 and the actuating element 15 and a further component for the outer sleeve 14.

What is claimed is:

1. A cartridge syringe (1) with a longitudinal opening (2) for inserting a cartridge (3), the cartridge (3) having an ampule cylinder (6) filled with a medication and the cylinder being closed at a front end by a piercing membrane (7) and at a rear end by a stopper (8), the stopper (8) having a blind hole (9), and a displaceably guided ram (13) at the rear end of a receptacle housing of the syringe (1), configured for pressing the stopper (8) for injecting the medication in the ampule cylinder (6) after piercing the piercing membrane (7), wherein a rear end of the ram (13) is provided with an actuating element (15) and a front end of the ram (13) is configured to be attached in the blind hole (9) of the stopper (8) for aspiration, the syringe characterized in that the ram (13) has an outer sleeve (14) in which a core (16) is disposed, wherein, at the rear end of the receptacle housing (1), the outer sleeve (14) is displaceably guided in a rotatable manner and the core (16) in a rotationally fixed manner, a front end of the outer sleeve (14) has, for the attachment in the blind hole (9) of the stopper (8), at least one fixing hook (22, 23) which is spring-loaded inwardly and which is movable between a fixing position in the blind hole (9) of the stopper (8) being directed outwardly sideways and an inwardly directed unlocked position, and, at a front end of the core (16), a cam (24) is provided, engaging with the fixing hook (22, 23) such that, upon rotation of the outer sleeve (14), the fixing hook (22, 23) is movable either to the fixing position or to the unlocked position.

2. A cartridge syringe according to claim 1, characterised in that two spring-loaded fixing hooks (22, 23) facing each other are provided and the cam (24) is elliptical in cross section, wherein the fixing hooks (22, 23) rotated about the major axis of the ellipse are rotated to the fixing position and the fixing hooks (22, 23) rotated to the minor axis of the ellipse are rotated to the unlocked position.

3. A cartridge syringe according to claim 1 characterized in that a slotted guide is provided for the rotation of the outer sleeve (14).

4. A cartridge syringe according to claim 3, characterized in that the slotted guide comprises a recess (25) on the outside of the outer sleeve (14), with a protrusion (26*a*, 26*b*) attached to the rear end of the receptacle housing (1) engaging therewith.

5. A cartridge syringe according to claim 1, characterized in that, in order to be guided in a rotationally fixed manner, the core (16) has a longitudinally extending rib (18) which is guided on both sides by protrusions (19*a*, 19*b*) at the rear end of the receptacle housing (1).

6. A cartridge syringe according to claim 1, characterized in that the syringe is made of a plastic material and configured as a disposable syringe.

7. A method comprising:
   in a multi-component injection molding process, injection molding a disposable, cartridge syringe (1) from a plastic material such that the cartridge syringe (1) has:
   a receptacle housing (1) with a longitudinal opening (2) being configured for insertion therethrough of a cartridge (3) having an ampule cylinder (6) filled with a medication and closed at a front end of the cylinder by a piercing membrane (7) and at a rear end of the cylinder by a stopper (8) having a blind hole (9); and
   a displaceably guided ram (13) at the rear end of a receptacle housing of the syringe (1), the displaceably guided ram being configured for pressing the stopper (8) and injecting the medication in the ampule cylinder (6) after piercing the piercing membrane (7) when the cylinder is inserted in the receptacle, the ram (13) having a rear end being formed with an actuating element (15) and a front end being configured for attachment with the blind hole (9) of the stopper (8), the ram (13) being formed with an outer sleeve (14) in which a core (16) is disposed, the outer sleeve (14) and core (16) being formed in a manner such that at the rear end of the receptacle housing (1), the outer sleeve (14) is displaceably guided in a rotatable manner and the core (16) is displaceably guided in a rotationally fixed manner, the outer sleeve (14) being formed with at least one fixing hook (22, 23) at a front end of the outer sleeve (14), the at least one fixing hook (22, 23) being configured for the attachment in the blind hole (9) of the stopper (8), the at least one fixing hook (22, 23) being spring-loaded inwardly and movable between a fixing position and an unlocked position relative to the blind hole (9) of the stopper (8), wherein in the fixed position, the at least one fixing hook (22,23) is directed outwardly sideways and wherein in the unlocked position, the at least one fixing hook is directed inwardly, the core (16) being formed with a cam (24) at a front end of the core (16), the cam (24) engaging with the fixing hook (22, 23) such that upon rotation of the outer sleeve (14), the fixing hook (22, 23) is movable one of the fixing position and the unlocked position.

8. The method according to claim 7, wherein the step of injection molding includes injection molding the receptacle housing (1) and the actuating element (15) at a first station (SP1), injection molding the outer sleeve (14) connecting the receptacle housing (1) to the actuating element (15) at a second station (SP2), wherein the outer sleeve (14) is injection-moulded from a plastic material which does not adhere to a plastic material of the receptacle housing 1 and the actuating element (15), and, at a third station (SP3), injecting molding the core (16) of the outer sleeve (14) from a plastic material which does not adhere to the plastic material of the outer sleeve (14).

\* \* \* \* \*